United States Patent
Yuan

(10) Patent No.: US 9,040,931 B1
(45) Date of Patent: May 26, 2015

(54) METHOD AND APPARATUS FOR IDENTIFYING CVD DIAMOND

(71) Applicant: Chih-Chung Yuan, Taipei (TW)

(72) Inventor: Chih-Chung Yuan, Taipei (TW)

( * ) Notice: Subject to any disclaimer, the term of this patent is extended or adjusted under 35 U.S.C. 154(b) by 0 days.

(21) Appl. No.: 14/485,820

(22) Filed: Sep. 15, 2014

(30) Foreign Application Priority Data

Dec. 11, 2013 (CN) .......................... 2013 1 0669193
Feb. 14, 2014 (CN) .......................... 2014 1 0051072

(51) Int. Cl.
*G01J 1/42* (2006.01)
*G01N 21/55* (2014.01)
*G01N 21/25* (2006.01)

(52) U.S. Cl.
CPC .............. *G01N 21/55* (2013.01); *G01N 21/255* (2013.01); *G01N 2201/08* (2013.01); *G01N 2201/061* (2013.01)

(58) Field of Classification Search
CPC .................................... G01J 1/42; G01N 21/55
USPC .................... 250/358.1, 370.01, 372
See application file for complete search history.

(56) References Cited

PUBLICATIONS

Dore et al. "Infrared proeprties of chemical-vapor deposition polycrystalline diamond windows", Applied Optics, vol. 37, No. 4, pp. 5731-5736, Aug. 20, 1998.*

* cited by examiner

*Primary Examiner* — David Porta
*Assistant Examiner* — Meenakshi Sahu

(57) ABSTRACT

Method for identifying CVD diamond comprises (1) placing a clean diamond on a fixed platform; (2) illuminating the diamond with light having various wavelengths; (3) receiving reflected light from the diamond; (4) calculating a reflectance value at each wavelength based on a light intensity at each wavelength of the reflected light, generating a spectral reflectance curve; (5) determining whether the spectral reflectance curve has a sharp trough, then storing the diamond if the spectral reflectance curve thereof does not have the sharp trough, while selecting the diamond for a further identification if the spectral reflectance curve thereof has the sharp trough; and (6) determining whether the sharp trough of the diamond selected from the step (5) is at a wavelength between 227 nm and 233 nm, and identifying the diamond to be the CVD diamond if the sharp trough is at the wavelength between 227 nm and 233 nm.

9 Claims, 1 Drawing Sheet

METHOD AND APPARATUS FOR IDENTIFYING CVD DIAMOND

CROSS-REFERENCE TO PRIOR APPLICATION

This application claims the benefit of Chinese Patent Application No. 201310669193.5, filed on Dec. 11, 2013 and Chinese Patent Application No. 201410051072.9, filed on Feb. 14, 2014, the entire content of which are incorporated herein by reference.

FIELD OF THE INVENTION

The present application relates to a method for identifying a diamond, and especially to a method and an apparatus for identifying a CVD diamond.

BACKGROUND OF THE INVENTION

Chemical vapor deposition (CVD) grown diamonds are moving into the international jewelry market recently. Since the qualities of CVD diamonds are very similar to that of highest-quality natural diamonds, it's difficult to distinguish the CVD diamonds from the natural diamonds. There is thus a growing sense of unease and worry among the customers and diamond dealers, which may lead to serious economic losses. Therefore, various methods for identifying CVD diamonds have been emerged, some widely-used methods are described as follows:

(1) Ultraviolet fluorescence identification method. Some of the natural diamonds emit fluorescence while some do not, but all the CVD diamonds emit special fluorescence. However, the special fluorescence of the CVD diamonds cannot be observed under long-wave ultraviolet light, and only under short-wave ultraviolet light can some weak fluorescence or very weak fluorescence be observed. Therefore, if an inspector has already worked for a long time, it's very likely that he will make a misjudgment.

(2) DiamondView detection method. In this method, a DiamondView monitor is used for identifying diamonds. During the detection, blue-green fluorescence and blue phosphorescence that reflect the specific texture characteristics of a CVD diamond can be observed. However, this method is still not effective to realize a heavy detection work.

(3) Photoluminescence identification method. In this method, a diamond is irradiated with Raman laser, and then an absorption peak at a wavelength of 737 nm can be observed in the stimulated emission spectrum. However, there isn't always an absorption peak in every CVD diamond' spectrum, the detection result is thus unreliable.

In order to help ensure the fairness and justice of the jewelry market, the inventor of the present application made a lot of experiments on various kinds of natural diamonds, man-made diamonds and optimized diamonds with UV-visible-NIR spectrometer. Surprisingly, the inventor found out that spectral reflectance curve of all the existing colorless or near colorless CVD has a sharp trough at a wavelength of about 230 nm. This is because CVD diamonds are grown in high concentrations of hydrogen under heat treatments, thereby forming C—H bonds. Due to the C—H bonds, the spectral reflectance curve of the CVD diamonds will show an absorption peak at the wavelength of about 230 nm.

SUMMARY OF THE INVENTION

The technical problem to be solved by the present invention is to provide a method and an apparatus for identifying a CVD diamond, which can distinguish the CVD diamonds from natural diamonds quickly and accurately.

In order to solve the above technical problem, an embodiment of the present invention provides a method for identifying a CVD diamond, which comprises the steps of: (1) placing a clean diamond on a fixed platform; (2) illuminating the diamond with light having various wavelengths; (3) receiving reflected light from the diamond; (4) calculating a reflectance value at each wavelength based on a light intensity at each wavelength of the reflected light, generating a spectral reflectance curve; (5) determining whether the spectral reflectance curve has a sharp trough, then storing the diamond if the spectral reflectance curve thereof does not have the sharp trough, while selecting the diamond for a further identification if the spectral reflectance curve thereof has the sharp trough; and (6) determining whether the sharp trough of the diamond selected from the step (5) is at a wavelength between 227 nm and 233 nm, and identifying the diamond to be the CVD diamond if the sharp trough is at the wavelength between 227 nm and 233 nm.

Preferably, in the step (2), the various wavelengths range from 200 nm to 450 nm.

Preferably, in the step (6), the diamond selected from the step (5) is identified to be the CVD diamond if the wavelength of the sharp trough is 230 nm.

Another embodiment of the present invention provides an apparatus for identifying a CVD diamond, which comprises: a light-emitting system for illuminating a diamond with light having various wavelengths; a light-receiving system for receiving reflected light from the diamond; a signal-converting system for converting an intensity of the reflected light received by the light-receiving system to a digital signal at each wavelength; and a processing system for processing the digital signal into a reflectance value, generating a spectral reflectance curve and determining whether the spectral reflectance curve has a sharp trough at a wavelength between 227 nm and 233 nm.

Preferably, the apparatus further comprises a displaying system which automatically displays an indication of CVD diamond when the processing system confirms that the spectral reflectance curve of the diamond has the sharp trough at the wavelength between 227 nm and 233 nm.

Preferably, the light having various wavelengths emitted by the light-emitting system has wavelengths ranging from 220 nm to 450 nm.

Preferably, the diamond to be identified is colorless or near-colorless.

Preferably, the light-receiving system comprises a probe lens and an optical fiber, wherein the probe lens is used for enlarging a light-collecting area, the fiber is used for transmitting a light signal, and the light-receiving system may be equipped with various types of the optical fiber.

Compared with the prior art, the method and the apparatus of the present invention have the following beneficial effects:

The method of the present invention detects the colorless or near colorless diamonds, obtains the spectral reflectance curve based on the intensity of the light, and determines whether there exists the sharp trough in the spectral reflectance curve, once the sharp trough appears at the wavelength between 227 nm and 233 nm, the diamond can be identified as a CVD diamond. The whole identification process takes only 1 second. Therefore, the method of the present invention can distinguish the CVD diamonds from a lot of natural diamonds quickly and efficiently. It not only simplifies the identification process, but increases the efficiency of market transactions as well, thereby ensuring the fairness and justice of the jewelry market.

The apparatus of the present invention illuminates the colorless or near colorless diamond with light having various optical wavelengths ranging from 200 nm-450 nm, and determines whether there exists the sharp trough at the wavelength between 227 nm and 233 nm in the spectral reflectance curve of the diamond. Since the light's wavelength band to be detected is limited to a narrower range of 227 nm to 233 nm, the use of the apparatus of the present invention not only reduces the time for the identification, but also reduces the error caused by a wide detected wavelength band. What's more, the apparatus of the present invention is an energy-saving equipment and is easy to manufacture, thereby lowing the cost. Besides, the apparatus of the present invention may be equipped with various types of the optical fiber, which makes it possible to identify a diamond as small as 0.0005 karat.

BRIEF DESCRIPTION OF THE DRAWINGS

To better describe the technical solutions in the embodiments of the present invention and the prior art, the following briefly introduces the accompanying drawings needed for describing the present invention and the prior art. Apparently, the accompanying drawings in the following description show some embodiments of the present invention, and persons of ordinary skill in the art may still derive other drawings from these accompanying drawings without creative efforts.

DETAILED DESCRIPTION OF ILLUSTRATED EMBODIMENTS

Various preferred embodiments will now be described with reference to the figures. Apparently, the embodiments to be described are merely a part rather than all of the embodiments of the present invention. All other embodiments obtained by persons of ordinary skill in the art based on the embodiments of the present invention without creative efforts shall fall within the protection scope of the present invention.

A method for identifying a CVD diamond, and especially for identifying whether a colorless or a near colorless diamond is a CVD diamond, comprises the following steps: (1) placing a clean diamond on a fixed platform; (2) illuminating the diamond with light having various optical wavelengths; (3) receiving reflected light from the diamond; (4) calculating a reflectance value at each wavelength based on a light intensity at each wavelength of the reflected light, generating a spectral reflectance curve; (5) determining whether the spectral reflectance curve has a sharp trough, then storing the diamond if the spectral reflectance curve thereof does not have the sharp trough, while selecting the diamond for a further identification if the spectral reflectance curve thereof has the sharp trough; and (6) determining whether the sharp trough of the diamond selected from the step (5) is at a wavelength between 227 nm and 233 nm, and identifying the diamond to be the CVD diamond if the sharp trough is at the wavelength between 227 nm and 233 nm.

In the step (2), the various wavelengths range from 200 nm to 450 nm.

It should be noted that, in the step (5), the diamond that doesn't have the sharp trough may be a natural diamond or other kind of artificial diamond.

Preferably, the step (6) further checks if the spectral reflectance curve has the sharp trough at the wavelength of 230 nm.

Figure 1:
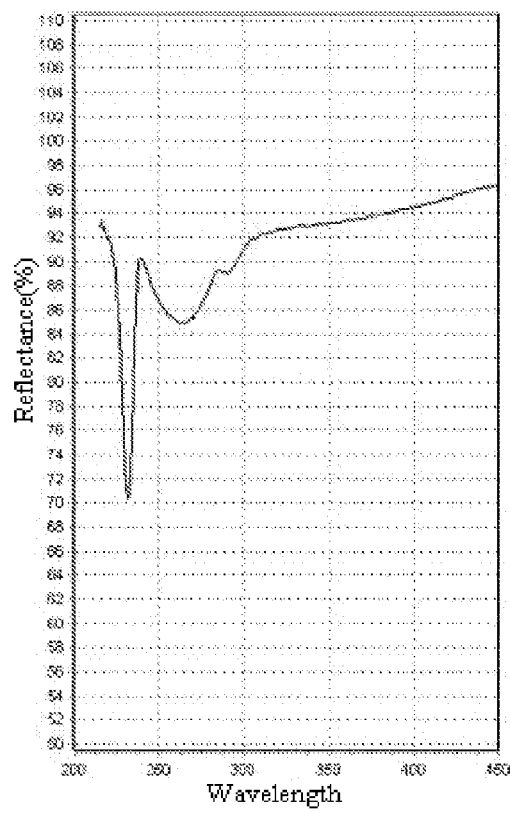
FIG. 1 shows a spectral reflectance curve of a CVD diamond according to an embodiment of a method for identifying a CVD diamond of the present invention, wherein a sharp trough exists at a wavelength of 230 nm.

In this embodiment, the method of the present invention detects the colorless or near colorless diamonds, obtains the spectral reflectance curve based on the intensity of the light, and determines whether there exists the sharp trough in the spectral reflectance curve, once the sharp trough appears at the wavelength between 227 nm and 233 nm, such as 230 nm as shown in FIG. 1, the diamond can be identified as a CVD diamond. The whole identification process takes only 1 second. Therefore, the method of the present invention can distinguish the CVD diamonds from a lot of natural diamonds quickly and efficiently. It not only simplifies the identification process, but increases the efficiency of market transactions as well, thereby ensuring the fairness and justice of the jewelry market.

Figure 2:
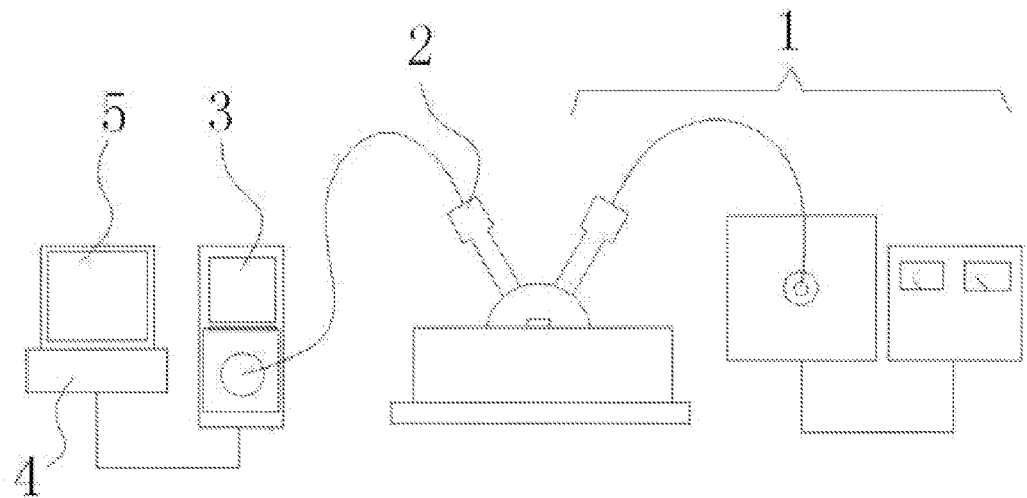
FIG. 2 is a structural schematic diagram of an apparatus of the present invention which is used in the embodiment of FIG. 1.

In another embodiment, as shown in FIG. 2, an apparatus suitable to carry out the method described in the above embodiments comprises: a light-emitting system 1 for illuminating a diamond with light having various wavelengths; a light-receiving system 2 for receiving reflected light from the diamond; a signal-converting system 3 for converting an intensity of the reflected light received by the light-receiving system 2 to a digital signal at each wavelength; and a processing system 4 for processing the digital signal into a reflectance value, generating a spectral reflectance curve and determining whether the spectral reflectance curve has a sharp trough at a wavelength between 227 nm and 233 nm.

In this embodiment, the apparatus of the present invention illuminates the colorless or near colorless diamond with light having various wavelengths ranging from 200 nm-450 nm, and determines whether there exists the sharp trough at the wavelength between 227 nm and 233 nm in the spectral reflectance curve of the diamond. Since the light's wavelength band to be detected is limited to a narrower range of 227 nm to 233 nm, the use of the apparatus of the present invention not only reduces the time for the identification, but also reduces the error caused by a wide detected wavelength band. What's more, the apparatus of the present invention is an energy-saving equipment and is easy to manufacture, thereby lowing the cost. Besides, a limitation of a wavelength band of the illuminating light to 227 nm-233 nm can further reduce the processing time and further increase the efficiency.

The apparatus described above further comprises a displaying system 5. The displaying system 5 automatically displays an indication of CVD diamond when the processing system 4 confirms that the spectral reflectance curve of the diamond has the sharp trough at the wavelength between 227 nm and 233 nm. With the help of the displaying system 5, identification result is visualized, which make it easier for the inspector to operate the apparatus and identify diamonds.

Furthermore, the light-receiving system 2 comprises a probe lens and an optical fiber (not shown in FIG. 1 or FIG. 2), the probe lens is used for enlarging the light-collecting area and the optical fiber is used for transmitting the light signal. The light-receiving system can be equipped with different types of the optical fiber to fit various situations, for example, fit for identifying a diamond as small as 0.0005 karat.

All the above are the preferred embodiments of the present invention. It is to be understood that, for one skilled in the art, the invention is intended to cover various modifications and equivalent arrangements included within the principle of the invention.

What is claimed is:

1. A method for identifying a CVD diamond, characterized in that, the method comprises the steps of:
   (1) placing a clean diamond on a fixed platform;
   (2) illuminating the diamond with light having various wavelengths;
   (3) receiving reflected light from the diamond;
   (4) calculating a reflectance value at each wavelength based on a light intensity at each wavelength of the reflected light, generating a spectral reflectance curve;
   (5) determining whether the spectral reflectance curve has a sharp trough, then storing the diamond if the spectral reflectance curve thereof does not have the sharp trough, while selecting the diamond for a further identification if the spectral reflectance curve thereof has the sharp trough; and
   (6) determining whether the sharp trough of the diamond selected from the step (5) is at a wavelength between 227 nm and 233 nm, and identifying the diamond to be the CVD diamond if the sharp trough is at the wavelength between 227 nm and 233 nm.

2. The method as claimed in claim 1, characterized in that, in the step (2), the various wavelengths range from 200 nm to 450 nm.

3. The method as claimed in claim 1, characterized in that, in the step (6), the diamond selected from the step (5) is identified to be the CVD diamond if the wavelength of the sharp trough is 230 nm.

4. The method as claimed in claim 2, characterized in that, in the step (6), the diamond selected from the step (5) is identified to be the CVD diamond if the wavelength of the sharp trough is 230 nm.

5. An apparatus for identifying a CVD diamond, characterized in that, the apparatus comprises:

a light-emitting system for illuminating a diamond with light having various wavelengths;

a light-receiving system for receiving reflected light from the diamond;

a signal-converting system for converting an intensity of the reflected light received by the light-receiving system to a digital signal at each wavelength; and a processing system for processing the digital signal into a reflectance value, generating a spectral reflectance curve and determining whether the spectral reflectance curve has a sharp trough at a wavelength between 227 nm and 233 nm.

6. The apparatus as claimed in claim 5, characterized in that, the apparatus further comprises a displaying system which automatically displays an indication of CVD diamond when the processing system confirms that the spectral reflectance curve of the diamond has the sharp trough at the wavelength between 227 nm and 233 nm.

7. The apparatus as claimed in claim 5, characterized in that, the light having various wavelengths emitted by the light-emitting system has wavelengths ranging from 220 nm to 450 nm.

8. The apparatus as claimed in claim 5, characterized in that, the diamond to be identified is colorless or near-colorless.

9. The apparatus as claimed in claim 5, characterized in that, the light-receiving system comprises a probe lens and an optical fiber, wherein the probe lens is used for enlarging a light-collecting area, the optical fiber is used for transmitting a light signal, and the light-receiving system may be equipped with various types of the optical fiber.

* * * * *